(12) United States Patent
Reynolds et al.

(10) Patent No.: US 8,034,373 B2
(45) Date of Patent: Oct. 11, 2011

(54) METHODS AND COMPOSITIONS FOR REDUCING OXIDATIVE STRESS IN AN ANIMAL

(75) Inventors: Arleigh J. Reynolds, Salcha, AK (US); Janet R. Jackson, Columbia, IL (US); Mark K. Waldron, Sunset Hill, MO (US)

(73) Assignee: Nestec S. A., Vevey (CH)

( * ) Notice: Subject to any disclaimer, the term of this patent is extended or adjusted under 35 U.S.C. 154(b) by 0 days.

(21) Appl. No.: 11/106,758

(22) Filed: Apr. 15, 2005

(65) Prior Publication Data

US 2005/0249788 A1   Nov. 10, 2005

Related U.S. Application Data

(60) Provisional application No. 60/562,815, filed on Apr. 16, 2004.

(51) Int. Cl.
*A23K 1/16* (2006.01)
*A61K 31/122* (2006.01)
*A61K 31/355* (2006.01)

(52) U.S. Cl. .......................... 424/442; 514/458; 514/691

(58) Field of Classification Search .................. 514/100, 514/691, 458
See application file for complete search history.

(56) References Cited

U.S. PATENT DOCUMENTS

| 6,022,867 | A * | 2/2000 | Ito et al. .......................... 514/100 |
| 6,265,450 | B1 * | 7/2001 | Asami et al. .................... 514/691 |
| 2003/0206972 | A1 * | 11/2003 | Babish et al. ................... 424/725 |
| 2004/0151761 | A1 | 8/2004 | Chew et al. ..................... 424/442 |
| 2004/0175413 | A1 * | 9/2004 | Sidebottom et al. ........... 424/442 |

FOREIGN PATENT DOCUMENTS

| EP | 0 628 258 A1 | 12/1994 |
| EP | 0 848 955 A1 | 6/1998 |
| JP | 2002080351 | 3/2000 |
| WO | 97/35491 A1 | 10/1997 |
| WO | 02/24002 A2 | 3/2002 |
| WO | 03/013268 A1 | 2/2003 |
| WO | 2004/071211 A1 | 8/2004 |
| WO | 2005/058064 A1 | 6/2005 |

OTHER PUBLICATIONS

Hinchcli FF et al Oxidant Stress in Sled Dogs—AJVR, vol. 61 # 5 May 2000 pp. 512-517.*
Babizhayev, et al., *Drugs R.D.*, 2004, 5(3), 125-139.
Derwent Publications, "Preparation astaxanthin contain powdery composition by drying and pulverize crustacean at 0-35 deg. C, useful as feed additive," JP1186346, 1988, XP-002342472, 1 page (abstract).
Halliwell, B., "Free radicals and antioxidants: a personal view," *Nutr. Rev.*, 1994, 52, 253-265.
Kang, J.O., et al., "Effect of astaxanthin on the hepatotoxicity, lipid peroxidation and antioxidative enzymes in the liver of CC14-treated rats," *Dept. of Pharmacology, School of Dentistry, Kyung Hee University*, S. Korea, 2001, 23(2), 79-84 (abstract, 1 page).
Reynolds, A.J., et al., *J. Nutr.*, 1994, 124(*12 Suppl.*), 2754S-2759S.
Tzu-Hua, W., et al., Annual Meeting of Professional Research Scientists on Experimental Biology, New Orleans, LA, Apr. 20-24, 2002, ISSN 0892-6638, Meeting Abstract, XP-002342435, 1 page.

* cited by examiner

*Primary Examiner* — Neil Levy
(74) *Attorney, Agent, or Firm* — Potter Anderson & Corroon LLP

(57) ABSTRACT

Methods for the reduction or prevention of oxidative stress in an animal comprising administering to the animal an effective amount of a composition comprising astaxanthin and/or Vitamin E are described. Also described are compositions comprising astaxanthin and/or Vitamin E, the compositions being effective for the reduction or prevention of oxidative stress in an animal.

3 Claims, No Drawings

METHODS AND COMPOSITIONS FOR REDUCING OXIDATIVE STRESS IN AN ANIMAL

CROSS-REFERENCE TO RELATED APPLICATIONS

This claims benefit of U. S. Provisional Application No. 60/562,815, filed Apr. 16, 2004, the disclosure of which is hereby incorporated by reference in its entirety. This also is related to U. S. Application Ser. No. 11/106,757, filed Apr. 15, 2005, now abandoned The entire contents of that application are also incorporated by reference.

FIELD OF THE INVENTION

This invention relates generally to methods and compositions effective in reducing and/or preventing oxidative stress in an animal by astaxanthin and/or Vitamin E supplementation.

BACKGROUND OF THE INVENTION

Cells obtain energy from the oxidation of a variety of organic molecules, and oxygen is the primary oxidant in the biochemical reactions that perform this function. Oxidative stress, which results from the metabolic reactions that use oxygen, may be considered a disturbance in the equilibrium status of pro-oxidant/anti-oxidant systems in intact cells. Cells have intact pro-oxidant/anti-oxidant systems that continuously generate and detoxify oxidants during normal aerobic metabolism. When additional oxidative events take place, the pro-oxidant systems outbalance those of the anti-oxidant, which may result in oxidative damage to cell components including lipids, proteins, carbohydrates, and nucleic acids. Mild, chronic oxidative stress may alter the anti-oxidant systems by inducing or repressing proteins that participate in these systems, and by depleting cellular stores of anti-oxidant materials such as glutathione and Vitamin E. Severe oxidative stress may ultimately lead to cell death.

An imbalance in pro-oxidant/anti-oxidant systems may result from a number of different oxidative challenges, including radiation, metabolism of environmental pollutants and administered drugs, as well as immune system response to disease or infection. The immune response is of particular significance since many toxic oxidative materials are generated in order to attack invading organisms. A variety of chemicals called radicals have roles in these processes. A radical species is any atom that contains one or more orbital electrons with unpaired spin states. A radical may be a small gas molecule such as oxygen or nitric oxide, or it may be a part of a large biomolecule such as a protein, carbohydrate, lipid, or nucleic acid. Some radical species are very reactive with other biomolecules and others, like the normal triplet state of molecular oxygen, are relatively inert.

Of interest with respect to oxidative stress are the reactions of partially reduced oxygen products and radical and non-radical species derived from them. A variety of reactive nitrogen species derived from the reactions of nitric oxide also play important roles in oxidative stress.

Oxidative stress has been implicated in human and animal disease. Cells have, however, multiple protective mechanisms against oxidative stress that act in preventing cell damage. Many dietary constituents are important sources of protective agents including anti-oxidant vitamins and minerals as well as food additives that might enhance the action of natural anti-oxidants. The effectiveness of an anti-oxidant in oxidative stress may be dependent on the specific molecules causing the stress, and the cellular or extracellular location of the source of these molecules.

Intense exercise can contribute significantly to oxidative stress in a number of ways. Most individuals have at some time in their lives experienced soreness and fatigue after physical exertion. For animals that undergo intense, frequent exercising, the effects of oxidative stress can have negative effects on performance.

Intense exercise results in a number of physiological changes in the body. First, aerobic respiration is dramatically increased, thereby increasing superoxide anion generation as much as 10-fold or more (Halliwell, B. (1994) Free radicals and antioxidants: a personal view. Nutr. Rev. 52:253-265), in addition to increasing exposure to environmental oxidative insults such as air pollution. Second, muscle and joint inflammation often result from intense exercise, thus triggering tissue infiltration of neutrophils and subsequent release of reactive oxygen species during the "oxidative burst" characteristic of activated neutrophils mediated by the immune response.

Enhanced antioxidant intake in humans has been reported to decrease the risk of developing specific forms of cancer and to enhance immune function. The effects of dietary antioxidant intake on pathological and physiological processes such as the aging process and exercise in dogs have been reported in the scientific literature. The effects of enhanced intakes of Vitamins E and C on immune function, free radical formation and free radical scrubbers have also been reported.

Cataracts may develop due to metabolic disorders such as diabetes, and from exposure to light, followed by subsequent oxidation of the lens. Oxidative stress, therefore, directly contributes to cataract formation. Primary (diene conjugates, cetodienes) lipid peroxidation (LPO) products accumulate during the initial stages of cataract formation while LPO fluorescent end-products are dominant in the later stages (Babizhayev et al. (2004) Drugs R. D. 5(3):125-139). Lens opacity correlates with the LPO fluorescent end-product accumulation in the tissue, and decreased reduced glutathione leads to sulfhydryl group oxidation of lens proteins (Babizhayev et al. (2004) Drugs R. D. 5(3):125-139). It has been shown that direct injection of LPO products into the vitreous induces cataract formation (Babizhayev et al. (2004) Drugs R. D. 5(3):125-139). Thus, peroxide damage of lens fiber membranes appears to initiate the development of cataracts (Babizhayev et al. (2004) Drugs R. D. 5(3):125-139).

Osteoarthritis (OA) is also related to oxidative stress. Free radicals, including nitric oxide, superoxide anion and hydrogen peroxide, lead to upregulation of enzymes responsible for damage to articular cartilage. These enzymes (MMPs) are specific for collagen, elastin and gelatin.

Oxygen radicals with unpaired electrons are produced as a normal part of oxygen metabolism. These reactive molecules may cause damage to, for example, proteins, nucleic acids (i.e., DNA) and/or membranes which may result in serious cell injury and disease in the whole animal. This process has been associated with the aging process, degenerative diseases, and cancer.

Animals that may be particularly vulnerable to oxidative damage or stress include those that are very active. For instance, well-conditioned canine athletes are healthy animals, which by virtue of their tremendous rates of oxygen consumption generate more free radicals each day than their more sedentary counterparts. The changes in immune function, metabolic intermediates, tissue stores of antioxidants and antioxidant enzymes induced by free radical production are greater in canine athletes than sedentary animals.

Previous studies examining hard working dogs revealed that exercise was associated with a significant increase in plasma concentrations of isoprostanes, a stable by product of lipid peroxidation. These same studies also demonstrated a decrease in plasma Vitamin E concentrations during exercise. Further studies examined the effect of Vitamin E supplementation on these parameters. Vitamin E supplementation helped decrease or alleviate the exercise associated drop in plasma Vitamin E concentration but did not decrease the elevations in plasma isoprostanes.

Astaxanthin is a mixed carotenoid which may be found in a number of sources; it is present in high levels in algae. This pigment protects the algal organism from damage due to ultraviolet radiation exposure. Several studies have demonstrated immuno-stimulatory properties of astaxanthin in cultured cells as well as whole animals (mice). It is also used in sunscreen lotions as it has been demonstrated to diminish reddening of the skin after sun exposure. Astaxanthin supplementation has also been associated with increased endurance in untrained human subjects.

SUMMARY OF THE INVENTION

In certain aspects, the present invention relates to methods for the reduction or prevention of oxidative stress in an animal comprising administering to the animal an effective amount of a composition comprising astaxanthin and/or Vitamin E. Additional aspects of the present invention relate to compositions comprising astaxanthin and/or Vitamin E, the compositions being effective for the reduction or prevention of oxidative stress in an animal.

In one aspect, the invention provides compositions comprising astaxanthin or astaxanthin and Vitamin E, and methods for the reduction or prevention of oxidative stress in an animal comprising administering to the animal an effective amount of a composition comprising astaxanthin or astaxanthin and Vitamin E. In some embodiments, the invention provides methods for treating an animal recovering from oxidative stress by administering an effective amount of a composition comprising astaxanthin or astaxanthin and Vitamin E.

In another aspect, the invention provides a method for evaluating the effect of a substance on oxidative stress in an animal comprising the steps of (a) administering the substance to the animal; (b) measuring one or more indices of oxidative stress in the animal prior to training; (c) training the animal according to an exercise regimen; (d) comparing the differences in the indices of oxidative stress in (b) and (d) to obtain at least one result; and (f) comparing the result obtained in (e) with the result obtained in a control animal which the substance is not administered; wherein the substance is deemed to have an effect on oxidative stress if the results obtained in (e) differ between those of the animal treated with the substance and those of the control animal.

In another aspect, the invention also provides methods for enhancing an immune response in an animal, reducing inflammation and pain associated with osteoarthritis in an animal and preventing or treating cataracts in an animal by administering an effective amount of a composition comprising astaxanthin or astaxanthin and Vitamin E.

Other features and advantages of the present invention will be understood by reference to the detailed description and the examples that follow.

DETAILED DESCRIPTION OF ILLUSTRATIVE EMBODIMENTS

Before describing the invention in detail, it should be understood that this invention is not limited to the particularly exemplified systems or process parameters as described in the specification for these parameters may of course vary. It is to be further understood that the terminology used herein is for the purpose of describing particular embodiments of the invention only, and is not intended to limit the scope of the invention in any manner for the invention in any manner.

As employed above and throughout the disclosure, the following terms, unless otherwise indicated, shall be understood to have the following meanings.

"Effective amount" refers to an amount of a compound, material, composition, and/or dosage form as described herein that may be effective to achieve a particular biological result. Such results may include, but are not limited to, reduction and/or prevention of oxidative stress. Such effective activity may be achieved, for example, by causing the ingestion of compositions according to aspects of the present invention.

"Mammal" refers to any of a class of warm-blooded higher vertebrates that nourish their young with milk secreted by mammary glands and have skin usually more or less covered with hair, and non-exclusively includes cats and dogs.

"Oxidative stress" refers to the condition characterized by an excess of oxidants and/or a decrease in antioxidant levels. Cellular oxidants may include, but are not limited to, one or more of: radicals of oxygen (superoxide anion, hydroxyl radical, and/or peroxy radicals); reactive non-radical oxygen species such as, for example, hydrogen peroxide and singlet oxygen; carbon radicals; nitrogen radicals; and sulfur radicals. The condition of oxidative stress may result in, for example, cellular damage, impaired performance of cells and/or cell death.

It must be further noted that as used in this specification and the appended claims, the singular forms "a," "an," and "the" include the plural referents unless the context clearly dictates otherwise.

In addition, the term "about" as used herein is intended to indicate a range of values of 10% greater and lesser than the indicated value. Thus, about 5% is intended to encompass a range of values from 4.5% to 5.5%.

Unless defined otherwise, all technical and scientific terms have the same meaning as commonly understood by one of ordinary skill in the art to which the invention pertains. Although a number of methods and materials similar or equivalent to those described herein can be used in the practice of the present invention, the preferred materials and methods are described herein.

All numerical ranges described herein include all combinations and subcombinations of ranges and specific integers encompassed therein.

According to certain aspects of this invention, exercise was utilized as a model to increase free radical production in an animal.

The present invention relates to any animal, preferably a mammal; more preferably to cats, and most preferably to dogs.

As used herein, "Vitamin E" refers to any of a group of related compounds with similar biological antioxidant activity, including alpha-tocopherol but also including other isomers of tocopherol and the related compound tocotrienol. The molecule is lipophillic and may reside in cell membranes. According to certain aspects of the invention, alpha-tocopherol may be a preferred form.

As used herein, "astaxanthin" refers to a mixed carotenoid occurring naturally in a wide variety of living organisms; it may also be produced synthetically. Sources of astaxanthin include, but are not limited to, crustaceans, including shrimp, crawfish, crabs and lobster; fish, including, for example, salmon; the pink yeast *Xanthophyllomyces*; and the microalga *Haematococcus pluvialis*. In certain preferred embodiments of the invention, the source of astaxanthin is NatuRose®, available from Cyanotech (Kailua-Kona, Hi.).

As used herein, a "foodstuff" refers to any substance that can be used or prepared for use as food. As used herein, a "food" is a material consisting essentially of protein, carbohydrate and/or fat, which is used in the body of an organism to sustain growth, repair and vital processes and to furnish energy. Foods may also contain supplementary substances such as minerals, vitamins and condiments. The term food includes a beverage adapted for human or animal consumption. As used herein, a "pharmaceutical" is a medicinal drug. A pharmaceutical may also be referred to as a medicament. As used herein, a "dietary supplement" is a product that is intended to supplement the diet; it may bear or contain any one or any combination of the following dietary ingredients: a vitamin, a mineral, an herb or other botanical, an amino acid, a dietary substance for use to supplement the diet by increasing the total daily intake (including, without limitation, enzymes or tissues from organs or glands), a concentrate, metabolite, constituent, or extract.

According to an embodiment of the present invention, a method is provided comprising the administration of astaxanthin and/or Vitamin E to an animal, the method being effective for the reduction and/or prevention of oxidative stress in the animal. According to an aspect of the invention, the method comprises the administration of an effective amount of astaxanthin. According to another aspect of the invention, the method comprises the administration of both astaxanthin and Vitamin E. Preferably, the astaxanthin and/or Vitamin E may be administered to an animal in a diet, food, foodstuff, dietary supplement, or pharmaceutical composition as, for example, described herein.

According to a preferred embodiment of the invention, the method is effective for facilitating oxidative stress recovery in animals. According to a particularly preferred embodiment, the method is effective for facilitating recovery from oxidative stress due to exercise.

The methods and compositions according to certain aspects of the invention may possess anti-aging effects in animals and therefore may be beneficial in promoting longevity of an animal. The compositions and methods of the invention are also useful in reversing, preventing or reducing detrimental conditions associated with oxidative stress, such as, but not limited to inflammation, osteoarthritis, cataract formation, weak immune systems, trauma, infection and premature aging. The compositions and methods are further useful in enhancing normal immune system function.

Without being limited by any theories or any particular modes of action of the invention, it is believed that the two antioxidants astaxanthin and Vitamin E may have differing efficacies against different types of oxidative stress. Vitamin E may be most effective against membrane lipid oxidation associated with exercise-induced elevations of oxygen metabolism. Astaxanthin may be most effective against oxidative stress caused by increased immune cell activity in the 24 hours following exercise. These observations suggest a potential for at least additive effects, and possibly synergism, if the two antioxidants are combined.

To illustrate certain aspects of the invention, Alaskan sled dogs ran 30 miles for three consecutive days and biomarkers, such as F-2 isoprostanes, were measured pre-, post-, 24 hr, and 48 hr after exercise. Because the rate of free radical generation in these exercising animals is greater than in the average household pet, the effect of years of free radical exposure was simulated in a short period of time: days to weeks. The blood analysis from these exercising dogs demonstrated significant declines in plasma Vitamin E and ceruloplasmin along with significant increases in isoprostanes, creatine kinase (CK) and uric acid (UA). When prostaglandins are exposed to free radicals they are converted into isoprostanes, which are stable for several hours and easily measured by a commercially available ELISA kit. Further, it has been shown that immune cell activity increases the concentration of lipid oxidation markers after exercise.

Three groups of twelve dogs (mixed breed Alaskan sled dogs (husky pointer crosses)) were fed commercially available Pro Plan® Performance chicken and rice formula dog food as a basal diet, and each group was fed either: a placebo consisting of about 0.5 g maltodextrin, about 2 mg astaxanthin, or about 400 mg Vitamin E (alpha-tocopherol). Pro Plan® dog food is available from Nestlé Purina Pet Care Company in St. Louis, Mo. The dogs were trained three times a week on an exercise wheel for a period of six weeks. On the sixth week, the dogs rested for four days and then exercised three days in a row. Blood samples were collected before exercise on day one, immediately after exercise on day three, and at 24 hours and 48 hours after exercise. Plasma from the blood samples was analyzed for concentrations of malondialdehyde, F-2 isoprostanes, Vitamin E, creatine kinase activity as well as oxygen radical absorption capacity (ORAC).

The effects of supplementing Vitamin E, astaxanthin, or a placebo on several indices of lipid oxidation and immune function were examined. Vitamin E was chosen because it is a common antioxidant and provided a benchmark upon which to compare other antioxidants. Astaxanthin is a mixed carotenoid which may be obtained from a number of sources, including, without limitation, being harvested from microalgae. It is soluble in both lipid and water compartments of the cell and therefore has a broader distribution than either Vitamin E (lipid soluble only) or Vitamin C (water soluble only). Astaxanthin has 4 times the in vitro oxygen radical absorptive capacity of Vitamin E. It is also reported to be more potent than Vitamin E or Vitamin C in preventing lipid peroxidation and scavenging free radicals.

According to certain aspects of the invention, dietary intake patterns of antioxidants, such as Vitamin E and astaxanthin, are identified. These antioxidants yield optimal protection from free radical induced changes in exercising dogs. By measuring each antioxidant individually and then in combination with others any additive or synergistic effects may be observed and antioxidant systems that may protect both the cell membrane and the cytosol may be developed.

According to an embodiment of the invention, a method of evaluating the effect of a composition on oxidative stress in an animal is provided comprising the steps of: a) administering the composition to the animal, b) measuring one or more indices of oxidative stress in the animal prior to training, c) training the animal according to an exercise regimen, d) measuring one or more indices of oxidative stress after training, e) comparing the differences in the indices of oxidative stress in b) and d) to similar differences in a control animal not administered the composition; wherein the composition is deemed to have an effect on oxidative stress if the result in e) differs between those of the animal treated with the composition and those of the control animal. Preferably, the exercise regimen involves training an animal on an exercise wheel, a treadmill and/or a swimming pool. The use of an exercise wheel enables the investigator to standardize the exertion of the animal by employing one or more settings corresponding to a fixed speed and distance. A treadmill may also enable such control and standardization by allowing the investigator to set parameters such as speed and inclination. A swimming regimen may also be standardized. Preferably, the indices of oxidative stress may be selected from one or more of: plasma concentration of malondialdehyde, plasma concentration of F-2 isoprostanes, plasma concentration of Vitamin E, creatine kinase activity, or oxygen radical absorption capacity (ORAC).

According to an embodiment of the present invention, a composition is provided comprising astaxanthin and/or Vitamin E, the composition being effective for the reduction and/or prevention of oxidative stress in animals. According to an aspect of the invention, the composition comprises an effective amount of astaxanthin. According to another aspect of the invention, the composition comprises astaxanthin and Vitamin E.

According to a preferred embodiment of the invention, the composition is effective for facilitating oxidative stress recovery in animals. According to a particularly preferred embodiment, the composition is effective for facilitating recovery from oxidative stress due to exercise. In other embodiments, the composition is effective for treating, delaying or preventing undesirable physiological conditions associated with oxidative stress. Examples include, but are not limited to osteoarthritis, cataract formation, reduced or compromised immune responses, and increasing the robustness of normal immune responses.

According to certain aspects of the invention, a composition of the invention may be useful as, for example, a diet, a food, a foodstuff, a dietary supplement, or a veterinary therapeutical product. The compositions may optionally contain a carrier, a diluent, or an excipient, chosen to be suitable for the intended use.

The compositions may be administered enterally, such as, for example, orally, intragastricly, or transpyloricly. Many factors that may modify the action of the composition can be taken into account by those skilled in the art; e.g., body weight, sex, diet, time of administration, route of administration, rate of excretion, condition of the subject, and reaction sensitivities and severities. Administration can be carried out continuously or periodically, such as once daily, or once with every meal.

Certain aspects of the invention are preferably used in combination with a complete and balanced food (for example, as described in National Research Council, 1985, Nutritional Requirements for Dogs, National Academy Press, Washington D.C., or Association of American Feed Control Officials, Official Publication 1996). That is, compositions comprising astaxanthin and/or Vitamin E according to certain aspects of this invention are preferably used with a high-quality commercial food. As used herein, "high-quality commercial food" refers to a diet manufactured to produce the digestibility of the key nutrients of 80% or more, as set forth in, for example, the recommendations of the National Research Council above for dogs. Similar high nutrient standards would be used for other animals.

The dosages of the substance(s) used in various aspects of the present invention that will be most suitable will vary with the form of administration, the particular substance(s) chosen and the physiological characteristics of the particular animal receiving the dose. According to certain aspects of the invention, preferred daily dosage ranges for Vitamin E may be from about 15 to about 500 mg per animal per day, more preferably from about 150 to about 450 mg per animal per day, more preferably about 400 mg per animal per day. Preferred daily dosage ranges for astaxanthin may be from about 0.001 to about 40 mg per animal per day. In some embodiments, the amount is from about 0.001 to about 10 mg per animal per day. In other embodiments the amount is from about 1 to about 40 mg per animal per day. In still other embodiments, the amount is from about 1 to about 20 mg per animal per day. In some preferred embodiments, the amount is from about 0.1 to about 8 mg per animal per day, more preferably about 2 mg per animal per day.

According to another aspect of the invention, there is provided a dietary supplement useful for the reduction and/or prevention oxidative stress in an animal, the supplement comprising astaxanthin and/or Vitamin E. The dietary supplement can be in any convenient form, including, without limitation, liquid, solid, or powder form. Solid forms of the supplement include, but are not limited to, a pill, biscuit, or treat.

According to certain embodiments of the invention, a dietary supplement can be formed as a foodstuff with higher levels of astaxanthin and/or Vitamin E which requires "dilution" before feeding to an animal. The supplement may be in any form, including, without limitation, solid (e.g. a powder), semi-solid (e.g. a food-like consistency/gel) or a liquid. The supplement may be administered to the animal in any suitable manner. For example, the liquid form can conveniently be mixed in with food or fed directly to the animal, such as, for example, via a spoon or via a pipe-like device. In certain embodiments, the supplement can be high in both components of astaxanthin and Vitamin E or can be a combined pack of two or more components, having the required concentrations of astaxanthin and/or Vitamin E separately or in any suitable combination.

EXAMPLES

The invention is further demonstrated in the following examples. Example 1 is an actual example and Examples 2-6 are prophetic examples. The examples are for purposes of illustration and are not intended to limit the scope of the present invention.

Example 1

Materials and Methods

All the dogs were maintained on the same basal diet (Purina Pro Plan® Performance chicken and rice formula) for one month prior to the onset and the entire duration of the experiment. Each dog was fed as an individual to maintain an optimal body condition score of 4/10. A body condition score of 4/10 indicates that the dogs were lean but not emaciated (1 is very thin, 10 is grossly obese).

Thirty-six sled dogs were housed at the Nestle Purina facility in Salcha, Ak. The dogs were divided into three groups of 12 dogs so that each group was alike in age, sex and ability distribution. A treatment was randomly assigned to each group by drawing from a hat. Group "A" was assigned about 400 mg Vitamin E/day, group "B" was assigned about 2 mg Astaxanthin/day and group "C" was assigned about 500 mg maltodextrin as a placebo. The people responsible for feeding, care, and training of the dogs were blind as to the identity of treatments until the completion of the study. Dogs were treated for six weeks before the onset of testing. They were also trained lightly for two sessions per week during this time period. Training sessions consisted of walking at 14 kilometers per hour for 2 hours in a 40-foot diameter circle tethered to a dog-walking wheel.

The testing took place over a six day period. On day one, pre-exercise blood samples were drawn from all the dogs. On day two, the dogs ran twelve km while pulling an all terrain vehicle (ATV) weighing 500 pounds. On day three, the dogs walked 16 miles on the dog wheel. On day four, the dogs again pulled the ATV for a distance of 12 kilometers. Immediately after exercise on day four, blood samples were drawn. Additional blood samples were drawn again at 24 hours and 48 hours after exercise. This sampling schedule was designed to examine changes in the parameters measured during exercise and during recovery. Samples were obtained by jugular venipuncture and collected into evacuated glass tubes containing sodium EDTA as an anticoagulant. Once collected they were kept on ice for not more than 10 minutes before they were centrifuged at 10,000 revolutions per minute (RPM) in 4° C. for a period of 10 minutes. The plasma was transferred into freezer vials where the dead space was replaced with gaseous nitrogen to decrease further oxidation during storage. The vials were then capped and immediately quenched in liquid nitrogen. The vials were recovered from liquid nitrogen and stored at −70° C. until analyzed. Each plasma sample was analyzed for malondialdehyde concentration using a standard HPLC, F2-isoprostane concentration utilizing a mass spectrometer and standard ELISA, Vitamin E concentration utilizing a standard HPLC, and Oxidative Radical Absorbance Capacity (ORAC test kit, Oxford Co.

F2 isoprostane and CK data was evaluated using a two way ANOVA for repeated measures. Post hoc comparisons were made using a student's t test corrected for repeated measures by the Bonneferroni method. Statistical significance was set at $p<0.05$. The other data was also evaluated using ANOVA. The abbreviation "se" used with respect to the data in the tables below refers to standard error.

Results

Plasma Vitamin E. Table 1 shows the plasma values for Vitamin E. Plasma Vitamin E concentrations were greatest for the Vitamin E treated group across all time periods. There was no significant difference between the plasma Vitamin E concentrations of Placebo and Astaxanthin (ATX) treated dogs for any time period. The plasma Vitamin E concentrations of all treatment groups tended to increase across time. All Vitamin E concentrations were maintained well above the minimum of the normal range for dogs established by the laboratory conducting the analyses.

TABLE 1

Plasma Vitamin E (mean +/− se)

| Time | Pre-ex | Post-ex | 24 hour post | 48 hour post |
|---|---|---|---|---|
| Placebo | 2170 (+/−404) | 1850 (+/−404) | 2380 (+/−404) | 2280 (+/−404) |
| ATX | 1635 (+/−358) | 1680 (+/−358) | 2000 (+/−358)* | 1990 (+/−358) |
| Vitamin E | 3370 (+/−390)a | 3540 (+/−390)*,a | 4720 (+/−390)*,a | 4520 (+/−390)*,a |

*= significantly different from pre exercise time period within the group
a= Significantly different than other treatment groups within the time period Plasma Malondialdehyde (MDA). Table 2 shows the values for plasma malondialdehyde. The only difference between the three treatment groups was observed at 24 hours post exercise where the Astaxanthin value was lower than either the placebo value or the Vitamin E value.

TABLE 2

Plasma MDA (mean +/− se)

| Time | Pre-ex | Post-ex | 24 hour post | 48 hour post |
|---|---|---|---|---|
| Placebo | 1.13 (+/−0.19) | 1.46 (+/−0.19) | 1.4 (+/−0.21) | 1.41 (+/−0.18) |
| ATX | 1.45 (+/−0.24) | 1.58 (+/−0.41) | 0.95 (+/−0.19)* | 1.44 (+/−0.19) |

TABLE 2-continued

Plasma MDA (mean +/− se)

| Time | Pre-ex | Post-ex | 24 hour post | 48 hour post |
|---|---|---|---|---|
| Vitamin E | 1.51 (+/−0.17) | 1.17 (+/−0.26) | 1.44 (+/−0.40) | 1.44 (+/−0.10) |

*= Significantly different from pre-exercise and post-exercise values within treatment group
a= Significantly different from placebo group within time period Table 3 shows the change in MDA from baseline for each time period. Relative to the pre-exercise value all post-exercise samples were elevated in the placebo group. There was no difference between the pre-exercise and post-exercise MDA values in the Astaxanthin group, but the 24-hour post-exercise value was significantly lower than the pre-exercise value. By 48 hours after exercise, the change in MDA values returned to baseline in this group. In the Vitamin E group the change in MDA values dropped from pre-exercise to post-exercise and returned to baseline in the 24 and 48-hour post exercise samples.

TABLE 3

Changes in Plasma MDA over time

| Change from Baseline | Pre to Post | Pre to 24 hour post | Pre to 48 hour Post |
|---|---|---|---|
| Placebo | +0.326* | +0.268* | +0.282* |
| ATX | 0.135 | −0.485* | −0.004 |
| Vitamin E | −0.336* | −0.071 | −0.069 |

*= Significantly different from baseline value within treatment group

Plasma F2-isoprostane (F2I). Table 4 shows the values for plasma F2I. There were no significant increases in plasma F2-isoprostane concentration between pre-exercise and post-exercise samples within any of the treatment groups. The placebo group showed an increase in F2I at 24 hours post-exercise; by 48 hours post-exercise the value had returned to the baseline value. F2I values in the Astaxanthin group dropped below the baseline value for immediate post-exercise, 24-hour post-exercise, and 48-hour post-exercise measurements. In the Vitamin E group F2I values for pre-exercise, post-exercise, and 24-hour post-exercise were not significantly different from each other. The value for 48 hours post-exercise was significantly lower than the other time periods for the Vitamin E treatment group.

Between the three groups there were several significant differences. Compared to the placebo group, the Astaxanthin group had lower F2I values immediately post-exercise and at 24 hours post-exercise. The value of Vitamin E F2I was not different from the placebo value except at the 24 hour post-exercise time period where it was lower. The only significant difference between Astaxanthin F2I values and Vitamin E F2I values occurred immediately after exercise. The Astaxanthin value was lower than the Vitamin E value for this time period.

TABLE 4

Plasma F2 Isoprostane concentration (mean +/− se)

| Time | Pre-ex | Post-ex | 24 hour post | 48 hour post |
|---|---|---|---|---|
| Placebo | 220 (+/−73) | 138 (+/−70) | 356 (+/−144)* | 186 (+/−110) |
| ATX | 167 (+/−111) | 52 (+/−13)*, a, b | 90 (+/−52)*, a | 66 (+/−21)* |

TABLE 4-continued

Plasma F2 Isoprostane concentration (mean +/- se)

| Time | Pre-ex | Post-ex | 24 hour post | 48 hour post |
|---|---|---|---|---|
| Vitamin E | 144 (+/-56) | 223 (+/-109) | 130 (+/-48) | 78 (+/-20)* |

*= significantly different than baseline value within treatment group
a= significantly different from placebo within same time period
b= significantly different from Vitamin E treatment group within the same time period Plasma Total Oxidative Radical Absorptive Capacity (ORAC). Table 5 shows the plasma values for total ORAC. In the placebo group, ORAC values increased from pre-exercise to post-exercise and remained elevated through 24 hours post-exercise. Placebo ORAC values returned to baseline values by 48 hours after exercise. There was no change in ORAC between pre-exercise and post-exercise in the Astaxanthin group. ORAC values fell below the baseline value in the 24-hour and 48-hour samples in the Astaxanthin group. In the Vitamin E group, the ORAC values fell from pre-to-post exercise, and then rose back to the baseline value at 24 hours post-exercise and then fell below baseline again at 48 hours post-exercise. The changes in plasma total ORAC values within treatments across time are similar to those obtained for MDA.

TABLE 5

Plasma total ORAC (mean +/- se)

| Time | Pre-ex | Post-ex | 24 hour post | 48 hour post |
|---|---|---|---|---|
| Placebo | 5430 (+/-408)a | 7330 (+/-408)* | 7790 (+/-408)* | 4950 (+/-408) |
| ATX | 7980 (+/-361) | 7460 (+/-361) | 5700 (+/-361)*, a | 4800 (+/-361) |
| Vitamin E | 7480 (+/-390) | 5850 (+/-390)*, a | 7590 (+/-390) | 4840 (+/-390) |

*= significantly different from baseline
a= significantly different from other treatments for this same time period Plasma Creatine Kinase (CK). Table 6 shows the plasma CK values. In all three groups the plasma CK values increased from pre-exercise to post-exercise and remained elevated for all remaining time periods. The Astaxanthin group also had lower CK values than the Vitamin E group for all time periods but 24 hours post-exercise where there was no significant difference between the two groups. None of the values measured in this experiment exceeded the normal range for CK.

TABLE 6

Plasma Creatine Kinase (mean +/- se)

| Time | Pre-ex | Post-ex | 24 hour post | 48 hour post |
|---|---|---|---|---|
| Placebo | 134 (+/-12) | 176 (+/-21)* | 220 (+/-50)* | 186 (+/-40)* |
| ATX | 109 (+/-11)a | 152 (+/-18)*, a | 171 (+/-24)* | 158 (+/-30)*, a |
| Vitamin E | 139 (+/-16)a | 208 (+/-16)* | 184 (+/-24)* | 204 (+/-25)* |

*= significantly different from baseline within the treatment group
a= significantly different from Vitamin E treatment group The Vitamin E-treated group maintained the greatest concentration of Vitamin E for each time period sampled. All groups showed an increase in plasma Vitamin E across time. This may be attributed to increased fat mobilization during exercise with concomitant incorporation of stored Vitamin E into circulating lipoproteins. It has previously been demonstrated that increases in plasma fatty acids and triglycerides in dogs during low level prolonged exercise were concomitant with increases in plasma Vitamin E. (Reynolds, A J, et al., *J Nutr.* 124(12 Suppl):2754S-2759S (1994). While the placebo and Astaxanthin groups maintained Vitamin E concentrations above the low normal limits established for dogs (below 60 would generally be considered somewhat low), the drop in MDA observed during exercise in the Vitamin E treated group suggests that there may be a benefit to supplementing Vitamin E above the baseline levels found in the diet.

The changes in MDA values suggest that Vitamin E supplementation may help protect against oxidative damage during exercise while Astaxanthin supplementation may protect against such damage during the first 24 hours of recovery from exercise. These findings suggest that these two antioxidants may have differing efficacies against different types of oxidative stress. Vitamin E may be most effective against membrane lipid oxidation associated with exercise-induced elevations of oxygen metabolism. Astaxanthin may be most effective against oxidative stress caused by increased immune cell activity in the 24 hours following exercise. These observations suggest a potential for synergism if the two antioxidants are combined.

Astaxanthin was found to protect the dogs from free radicals during immediate post exercise and up to 24 hours after exercise. Astaxanthin helped protect against peroxidative damage as measured by F2I during exercise and for the first 24 hours of recovery. Vitamin E treated dogs also showed improvement over placebo fed dogs at 24 hours post-exercise. F2I measures lipid peroxidation from sources other than those measured by MDA. The F2I data collected here suggests that Astaxanthin may better protect immune cells and sub cellular organelles during exercise than Vitamin E. Since F2I are byproducts of immune cells, the timing of the protection of the Astaxanthin suggests that much of its effects are mediated through modulation of immune cell function.

Both Astaxanthin and Vitamin E groups showed a decrease in ORAC during the time periods when these treatments were most successful in inhibiting lipid peroxidation. One reason the Vitamin E and Astaxanthin ORAC values dropped during exercise and at 24 hours post-exercise, respectively, may be that the supplemented antioxidants may have been consumed to contain lipid peroxidation during these time periods.

The fact that CK values were the lowest in the Astaxanthin group for nearly all measurements suggests that this supplement is protecting the muscle cell membranes from damage during exercise better than either Vitamin E or the placebo. The exercise in this study did not induce elevations in plasma CK above the normal range.

Compared to the placebo group, both Vitamin E and astaxanthin treatment showed improved protection against the oxidative stress associated with exercise. Vitamin E appears to be most effective against malondialdehyde production during exercise and most effective against F-2 isoprostane production during the first 24 hours after exercise. Astaxanthin supplementation was better at decreasing MDA production during the first 24 hours after exercise and better at curbing isoprostane production during exercise and the first 24 hours of recovery. These findings suggest that Vitamin E and Astaxanthin act in different cellular compartments and or pathways from each other. They also indicate a potential for at least an additive effect, and possibly a synergistic effect, if the two are combined.

Vitamin E supplementation resulted in decreased malondialdehyde concentrations during exercise when compared to the placebo group. Astaxanthin supplementation was associated with a decrease in malondialdehydes 24 hours post-exercise when compared to Vitamin E and placebo groups. ORAC (Oxygen Radical Absorption Capacity, which is an index of total anti-oxidant status) was not improved by either Vitamin E or astaxanthin supplementation for any of the time periods measured. Creatine kinase activity (an index of muscle cell membrane damage) and F-2 isoprostane (a measure of lipid oxidation from prostaglandins) concentrations only showed significant differences in the astaxanthin treated group and only in the immediate post-exercise and 24 hour post-exercise samples where they were lower than values measured in either Vitamin E or placebo groups. These findings indicate that both astaxanthin and Vitamin E show some protective effect against oxidative damage in exercising dogs. Astaxanthin showed a broader range of protection across a greater time period than Vitamin E. The results described herein suggest that a combination of Vitamin E and astaxanthin may have an effect that is at least additive and may be synergistic. It is thus recommended that astaxanthin be included in diets intended for dogs that may experience oxidative stressors including, but not limited to, exercise, infection, or trauma.

Example 2

Animals are administered a composition comprising a combination of astaxanthin and Vitamin E (alpha-tocopherol) to determine the effect on oxidative stress due to exercise.

Dogs are maintained on the same basal diet (Purina Pro Plan® Performance chicken and rice formula) for one month prior to the onset and the entire duration of the treatment. Two groups of dogs can be fed commercially available Pro Plan® Performance chicken and rice formula dog food as a basal diet, and each group is fed either: a placebo consisting of about 0.5 g maltodextrin, or a combination of about 2 mg astaxanthin and about 400 mg Vitamin E (alpha-tocopherol). Pro Plan® dog food is available from Nestle Purina Pet Care Company in St. Louis, Mo. The dogs are trained three times a week on an exercise wheel for a period of six weeks. On the sixth week, the dogs rest for four days and then exercise three days in a row. Blood samples are collected before exercise on day one, immediately after exercise on day three, and at 24 hours and 48 hours after exercise. Plasma from the blood samples are analyzed for concentrations of malondialdehyde, F-2 isoprostanes, Vitamin E, creatine kinase activity as well as oxygen radical absorption capacity (ORAC). Decreases in measures of oxidative stress and/or increases in measures of antioxidant status is indicative of anti-oxidative effects of a given treatment.

Example 3

An in vitro experiment may be performed using canine lens epithelial cells supplemented with astaxanthin at physiological levels. The studies would demonstrate that astaxanthin can significantly reduce free radical formation and lipid peroxidation products in canine lens epithelia when stressed with ultraviolet (UV) light. Additionally, when the astaxanthin supplemented canine lens epithelial cells are stressed with UV light, there would be significantly less cell death. The results would indicate that a decrease in free radical formation and lipid peroxidation products along with the decrease in cell death show that astaxanthin supplementation reduces the risk or severity of cataract formation in dogs.

Example 4

An in vivo study could also be performed to demonstrate the beneficial effects of astaxanthin in combating cataract formation. In a model study, 40 dogs could be chosen and randomly allocated to either the control group or to a treatment group receiving AAFCO recommended levels of antioxidants. The treatment group would receive astaxanthin and may also receive one or more of Vitamin E, lutein, zeaxanthin and zinc. At the conclusion of the treatment times (a two year study, for example), it would be shown that the control group has significantly more cataract formation and the severity of cataract would be significantly greater as assessed by a slit-lamp test.

Example 5

In vitro experiments may be performed to demonstrate that astaxanthin improves or enhances immune system function. In vitro assays to assess immune function are well-known to those of skill in the art. Many protocols are known and may be used to perform such assessments of immune function. Examples of such protocols are available in various journal articles and texts (e.g., Current Protocols in Immunology, John E. Coligan, Ada M. Kruisbeek, David H. Margulies, Ethan M. Shevach, Warren Strober, eds. John Wiley & Sons, NY 1999.

To assess the effect of astaxanthin supplementation on immune function, dogs may be fed a diet containing astaxanthin and/or Vitamin E for 16 weeks. The amount of astaxanthin used may be 0, 1, 5, 10, 20, and 40 mg per animal per day. Various assays may be performed to assess immune function.

In one assay, for example, peripheral blood mononuclear cells (PBMCs) may be stimulated in vitro with a polyclonal antisera, or Concanavalin A (ConA), phytohemagglutinin (PHA) or pokeweed mitogens. Lymphoproliferation is assessed by any known method.

In another in vitro lymphoproliferation test, astaxanthin may be added directly to the media of PBMC culture during stimulation to demonstrate that astaxanthin increases proliferation of cells significantly more than the proliferation observed in the absence of astaxanthin.

In another assay, natural killer (NK) cell cytotoxicity is assessed for NK cells isolated from animals that are fed a diet including astaxanthin supplementation. The NK cell assay would demonstrate that NK cytotoxicity is significantly increased in animals fed a diet containing astaxanthin as opposed to control animals not fed astaxanthin.

Delayed-type hypersensitivity may also be assessed in animals given a diet supplemented with astaxanthin. In these assays, control animals and animals fed a diet containing astaxanthin are given cutaneous injections of saline, a mitogen or a vaccine of distemper virus. The animals are then assessed to measure the skin reactions to mitogen, virus and control. In animals fed a diet containing astaxanthin, the skin reactions are more robust for virus and mitogen than that found in control animals.

Control animals and animals fed a diet containing astaxanthin may also be assessed for the robustness of the immune response against an antigen. For example, antibody titers against an antigen may be measured for control animals and animals fed a diet containing astaxanthin. Animals fed a diet containing astaxanthin would have higher antibody titers than control animals.

Example 6

Osteoarthritis (OA) is also associated with oxidative stress. OA is characterized by damage to the articular cartilage. This damage is mediated by enzymes (MMPs) that are specific for collagen, elastin and gelatin. Upregulation of these enzymes has been shown to be caused by free radicals including, but not limited to nitric oxide, superoxide anion, and hydrogen peroxide.

A diet supplemented with astaxanthin may be shown to reduce inflammation and associated pain in osteoarthritis. A study to demonstrate the beneficial effects of astaxanthin in the diet could be performed by randomly assigning a group of 24 dogs to either a control group or a group fed a diet containing astaxanthin at 1, 5, 10, 20, or 40 mg per animal per day. At 12 weeks of treatment, plasma and synovial fluid samples are taken from each animal and assayed for total antioxidant activity, and levels of malionaldehyde, prostaglandin, isoprostanes, MMPs and TIMPs. Additionally, the gait of the dogs may be assessed using standard force plate analyses. Biochemical analyses would show that astaxanthin supplementation results in a decrease in isoprostanes, total antioxidant activity and MMPs (in both plasma and synovial fluid. Treated dogs would show significant improvement in gait when compared to controls. The results would show that astaxanthin improves or delays the progression of OA in dogs.

The disclosures of each patent, patent application and publication cited or described in this document are hereby incorporated herein by reference, in their entirety.

Without departing from the spirit and scope of this invention, one of ordinary skill can make various changes and modifications to the invention to adapt it to various usages and conditions, mutatis mutandis. As such, these changes and modifications are properly, equitably, and intended to be, within the full range of equivalence of the following claims.

What is claimed:

1. A method for the reduction of oxidative stress due to exercise in a dog or cat, comprising administering to the dog or cat an antioxidant composition consisting essentially of an effective amount of astaxanthin and an effective amount of one or more of alpha-tocopherol and an isomer of tocopherol, wherein the astaxanthin and the one or more of alpha-tocopherol and an isomer of tocopherol are regularly administered to the dog or cat beginning about six weeks or more prior to the exercise.

2. A method of treating a dog or cat recovering from oxidative stress due to exercise, comprising administering to the dog or cat an antioxidant composition consisting essentially of an effective amount of astaxanthin and an effective amount of one or more of alpha-tocopherol and an isomer of tocopherol, wherein the astaxanthin and the one or more of alpha-tocopherol and an isomer of tocopherol are regularly administered to the dog or cat beginning about six weeks or more prior to the exercise.

3. A method of treating a dog or cat for oxidative stress due to exercise, consisting essentially of the steps of:
   a) regularly administering to the dog or cat an amount of astaxanthin, beginning about six weeks or more prior to the exercise; and
   b) regularly administering to the dog or cat an amount of one or more of alpha-tocopherol and an isomer of tocopherol, beginning about six weeks or more prior to the exercise;
   wherein the amounts of the astaxanthin and the amounts of the one or more of alpha-tocopherol and an isomer of tocopherol combined together are effective to treat the oxidative stress.

* * * * *